(12) United States Patent
Lee et al.

(10) Patent No.: US 8,124,016 B2
(45) Date of Patent: *Feb. 28, 2012

(54) ARTICLES WITH ANTIMICROBIAL PROPERTY AND MANUFACTURING METHOD THEREOF

(75) Inventors: Sung-Hwan Lee, Changwon-si (KR); Ok-Chun Hyun, Busan (KR); Hyung-Ho Park, Daejeon (KR)

(73) Assignee: LG Electronics, Inc., Seoul (KR)

( * ) Notice: Subject to any disclaimer, the term of this patent is extended or adjusted under 35 U.S.C. 154(b) by 958 days.

This patent is subject to a terminal disclaimer.

(21) Appl. No.: 12/084,580

(22) PCT Filed: Nov. 15, 2006

(86) PCT No.: PCT/KR2006/004816
§ 371 (c)(1),
(2), (4) Date: May 6, 2008

(87) PCT Pub. No.: WO2007/058476
PCT Pub. Date: May 24, 2007

(65) Prior Publication Data
US 2009/0151571 A1    Jun. 18, 2009

(30) Foreign Application Priority Data

Nov. 15, 2005  (KR) .................. 10-2005-0109351
Nov. 15, 2005  (KR) .................. 10-2005-0109352
Nov. 23, 2005  (KR) .................. 10-2005-0112626

(51) Int. Cl.
*B05D 1/36* (2006.01)
*B01D 41/00* (2006.01)
*B01D 39/14* (2006.01)

(52) U.S. Cl. ............. 422/120; 55/524; 96/223; 96/226; 427/196; 427/202; 427/203; 422/28

(58) Field of Classification Search .............. 96/226; 210/501; 422/4, 28, 59, 120, 121; 424/93.4, 424/93.45; 427/203, 421, 421.1, 427.4, 430.1, 427/196
See application file for complete search history.

(56) References Cited

U.S. PATENT DOCUMENTS 2,813,059 A * 11/1957 Davis et al. .................. 424/618
(Continued)

FOREIGN PATENT DOCUMENTS
EP         1369045        12/2003
(Continued)

OTHER PUBLICATIONS

Database WPI Week 200335 Thomson Scientific, London, GB; AN 2003-368966, XP002499635, KR 2002 091 498A (Pulmuwon Co. Ltd.) Dec. 6, 2002 Abstract.
(Continued)

*Primary Examiner* — Duane Smith
*Assistant Examiner* — Sonji Turner
(74) *Attorney, Agent, or Firm* — McKenna Long & Aldridge LLP (57) ABSTRACT

The present invention discloses an article with an antimicrobial property, and a manufacturing method thereof which gives the antimicrobial property to a surface of the article in which bacteria or viruses may contact to proliferate themselves. The antimicrobial property is obtained by coating Kimchi lactic acid bacteria culture fluid with a wide antibacterial spectrum singly or in combination with nano metal particles on the surface of the article.

24 Claims, 2 Drawing Sheets

U.S. PATENT DOCUMENTS

| | | | | |
|---|---|---|---|---|
| 2,880,129 | A * | 3/1959 | Billings | 427/430.1 |
| 4,740,593 | A * | 4/1988 | Gonzalez et al. | 422/1 |
| 4,980,163 | A * | 12/1990 | Blackburn et al. | 424/94.63 |
| 5,135,910 | A * | 8/1992 | Blackburn et al. | 514/2.8 |
| 5,217,950 | A * | 6/1993 | Blackburn et al. | 514/2.4 |
| 5,260,271 | A * | 11/1993 | Blackburn et al. | 514/2.6 |
| 5,458,906 | A * | 10/1995 | Liang | 427/2.31 |
| 5,573,797 | A * | 11/1996 | Wilhoit | 426/106 |
| 5,573,800 | A * | 11/1996 | Wilhoit | 426/326 |
| 5,573,801 | A * | 11/1996 | Wilhoit | 426/326 |
| 5,616,338 | A | 4/1997 | Fox, Jr. et al. | |
| 5,691,301 | A * | 11/1997 | Blackburn et al. | 514/2.4 |
| 5,753,614 | A * | 5/1998 | Blackburn et al. | 514/2.6 |
| 5,876,489 | A * | 3/1999 | Kunisaki et al. | 96/226 |
| 6,762,339 | B1 * | 7/2004 | Klun et al. | 602/58 |
| 2004/0121077 | A1 * | 6/2004 | Park et al. | 427/383.1 |
| 2004/0241216 | A1 * | 12/2004 | Klun et al. | 424/445 |
| 2006/0219641 | A1 * | 10/2006 | Kepner et al. | 210/723 |
| 2009/0151571 | A1 | 6/2009 | Lee et al. | |

FOREIGN PATENT DOCUMENTS

| | | | |
|---|---|---|---|
| FR | 2855181 | * | 11/2004 |
| KR | 10-2002-0091498 | | 12/2002 |
| KR | 2004000623 | * | 1/2004 |
| KR | 10-2005-0087742 | | 8/2005 |
| KR | 10-2005-0094654 | | 9/2005 |
| WO | WO 03/053397 A1 | | 7/2003 |
| WO | WO 2004/101011 A1 | | 11/2004 |
| WO | WO 2004/105822 A1 | | 12/2004 |
| WO | WO 2004/106481 A2 | | 12/2004 |
| WO | WO 2005/115151 A1 | | 12/2005 |
| WO | WO 2006/009394 A1 | | 1/2006 |
| WO | WO 2006/009395 A1 | | 1/2006 |

OTHER PUBLICATIONS

Park et al. "Identification and Characteristics of Nisin Z-Producing *Lactococcus lactis* subsp. *lactis* Isolated from Kimchi", Current Microbioloby, vol. 46, pp. 385-388, 2003, XP009129736.

* cited by examiner

Figure 1

An article

Coated with

Kimchi lactic acid bacteria culture fluid

Figure 2

ARTICLES WITH ANTIMICROBIAL PROPERTY AND MANUFACTURING METHOD THEREOF

This application claims the benefit of Korean Patent Application No. 10-2005-0109352, filed on Nov. 15, 2005; Korean Patent Application No. 10-2005-0109351, filed on Nov. 15, 2005; Korean Patent Application No. 10-2005-0112626, filed on Nov. 23, 2005 and PCT Application No. PCT/KR2006/004816, filed on Nov. 15, 2006, which is hereby incorporated by reference for all purposes as if fully set forth herein.

TECHNICAL FIELD

The present invention relates to an article with an antimicrobial property and a manufacturing method thereof.

BACKGROUND ART

Recently, with the increasing interest in the hygiene and cleanliness, a number of products have been developed to improve the hygiene and cleanliness. The electronic product field is not an exception. In detail, electric home appliances needing the hygiene and cleanliness include a refrigerator, washing machine, drying machine, air conditioner, air freshener, fan, cleaner, electric pot, electric cooker, dishwashing machine, dish drying machine, microwave oven, mixer, VTR, television, home theater, etc.

Bacteria or fungi which can be parasitic on the surfaces of the products or the surfaces of the components thereof cause diseases such as atopic dermatitis, respiratory trouble, etc., disfigure the products, generate a bad smell, and and maintaining the external appearances of the products, and this can be achieved by preventing the contact and proliferation of various bacteria and fungi.

Generally, most of antibacterial agents for manufacturing an antibacterial article are chemically synthesized, and the antibacterial agents are expensive and cause harmful side effects. Recently, researches have been actively made on a natural antibacterial material which has an excellent antibacterial property and no side effects harmful for a human body.

Kimchi lactic acid bacteria are generated in fermentation and mature of Kimchi. Safety of the Kimchi lactic acid bacteria as the natural source has been verified by the long time use. It is easy to acquire the Kimchi lactic acid bacteria at a low cost. In addition, the Kimchi lactic acid bacteria are known as a natural antibacterial material with an excellent antibacterial property and a wide antibacterial spectrum. Moreover, there has been reported that the Kimchi lactic acid bacteria culture fluid could inhibit activities of avian influenza viruses and other similar viruses.

Accordingly, the present inventors have accomplished this invention by coating the antimicrobial property to a surface of an article and using the antibacterial and antivirus effects of the Kimchi lactic acid bacteria culture fluid.

DISCLOSURE OF THE INVENTION

An object of the present invention is to provide an article with an antimicrobial property coated with the Kimchi lactic acid bacteria culture fluid having antibacterial and antivirus effects.

Another object of the present invention is to provide a manufacturing method of an article having an antimicrobial property which coats the Kimchi lactic acid bacteria culture fluid with antibacterial and antivirus effects on the surface of the article.

In order to achieve the above-described objects of the invention, there is provided an article with an antimicrobial property, which is coated with the Kimchi lactic acid bacteria culture fluid, or both the Kimchi lactic acid bacteria culture fluid and nano metal particles.

There is also provided a manufacturing method of an article with an antimicrobial property, the method including a step for coating the Kimchi lactic acid bacteria culture fluid or both the Kimchi lactic acid bacteria culture fluid and nano metal particles on the surface of the article.

BRIEF DESCRIPTION OF THE DRAWINGS

For a better understanding of the invention, reference may be made to the following description of exemplary embodiments taken in conjunction with the accompanying drawings, in which.

BEST MODE FOR CARRYING OUT THE INVENTION

An article with an antimicrobial property and a manufacturing method thereof in accordance with preferred embodiments of the present invention will now be described in detail.

Figure 1:
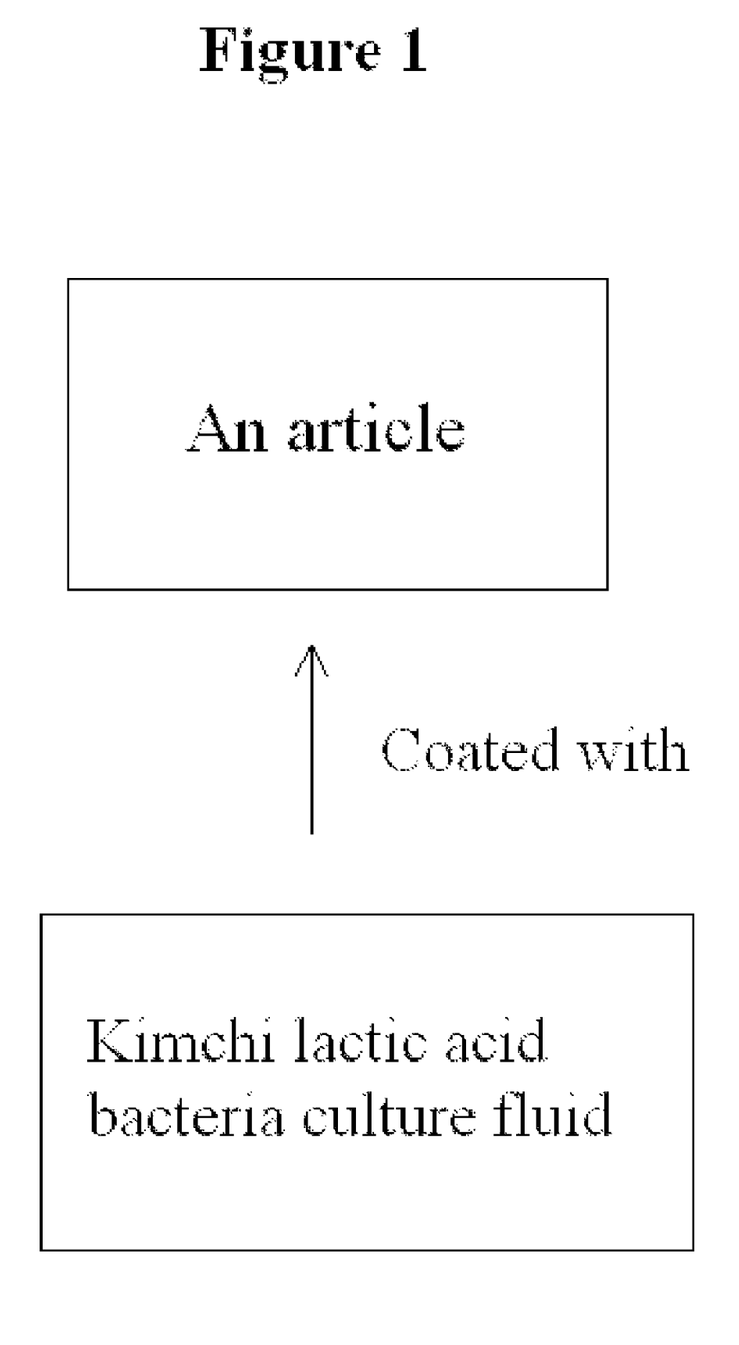
FIG. 1 is a diagram of an article coated with Kimchi lactic acid bacteria culture fluid.
Figure 2:
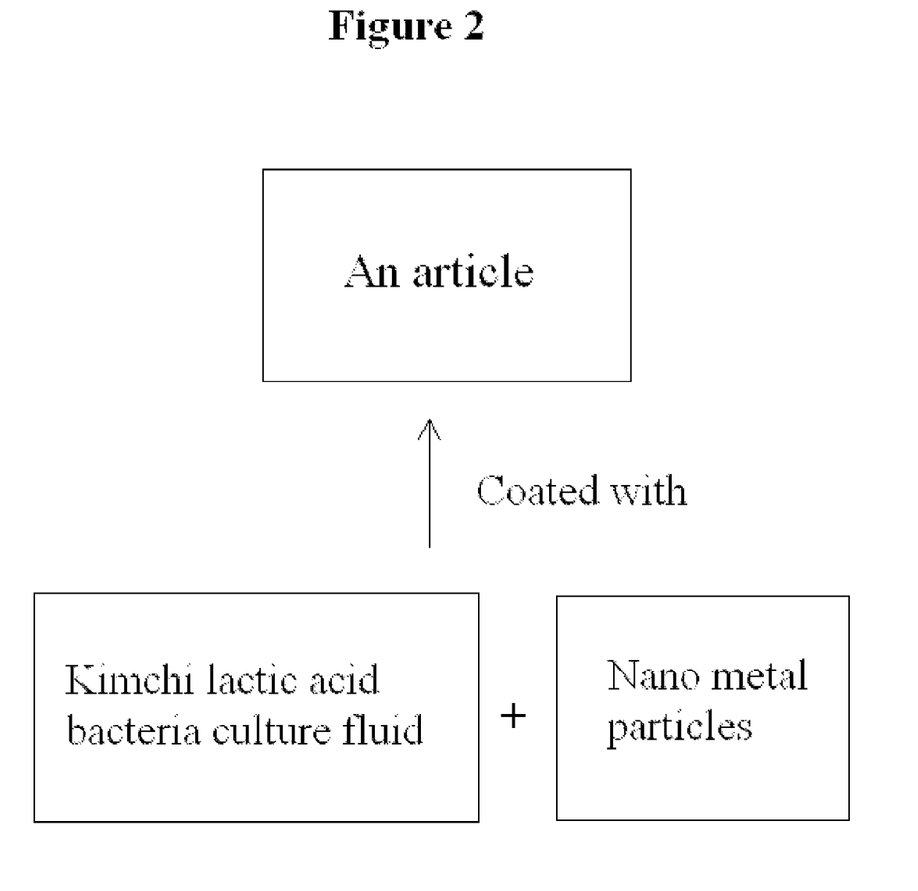
FIG. 2 is a diagram of an article coated with both Kimchi lactic acid bacteria culture fluid and nano metal particles.

The present invention provides the article coated with the Kimchi lactic acid bacteria culture fluid or both the Kimchi lactic acid bacteria culture fluid and nano metal particles. FIG. 1 is a diagram showing the article coated with Kimchi lactic acid bacteria culture fluid. FIG. 2 is a diagram showing the article coated with both Kimchi lactic acid bacteria culture fluid and nano metal particles.

Here, the antimicrobial property includes an antibacterial property, an antifungal property and an antivirus property.

The article means all kinds of articles which bacteria, viruses, etc. may contact to proliferate themselves without special restrictions in use of the article. Therefore, the article can be manufactured by a method publicly known in this field, for example, injection molding, extrusion molding, blow molding and thermal molding.

In accordance with one aspect of the present invention, the article can be one of electric home appliances. The electric home appliances mean the whole electric home appliances or the internal or external parts thereof. Exemplary electric home appliances include refrigerator, washing machine, drying machine, air conditioner, air freshener, fan, cleaner, electric pot, electric cooker, dishwashing machine, dish drying machine, water purifier, microwave oven, mixer, VTR, television and home theater. The parts of the electric home appliances are varied according to the kinds of the electric home appliances. For example, the parts of the washing machine are an inner tub, an outer tub, a detergent box, a drum lift, a water supply/drain passage, a filter, etc., the parts of the refrigerator are an inner/outer wall, a cool air duct, a ventilation fan, a door handle, a vegetable box, an ice maker, a filter, etc., and the parts of the air conditioner are an electric heat exchanger, a ventilation fan, an air passage, a filter, etc. Any kinds of raw materials which can form the whole electric home appliance or the forming member thereof can be used without special restrictions. For example, thermoplastic resin, thermosetting resin, rubber and metal can be used as the raw materials. The raw materials can be used in various ways according to their characteristics.

In accordance with another aspect of the present invention, the article can be a filter. Any article performing the filtering function can be used without special restrictions in use, kind and type. Exemplary articles include an air filter, a water filter and a cleaner filter. Any kinds of materials having the filtering function can be used as a material of the filter without special restrictions in kind, type, size and manufacturing process. Exemplary materials include a glass fiber, an ion exchange fiber, a cellulose fiber and an asbestos fiber, various organic and inorganic fibers, a metal such as zinc, copper and aluminum, and a plastic. Such materials can be variously used depending on their characteristics. The type of the filter can be appropriately modified depending on an apparatus using the filter without special restrictions, such as honeycomb type, grain type, net type, filter paper type, cotton type, mesh type, plate type and foam type. In accordance with the present invention, the filter can be used singly or in combination with the existing filter in the same product.

In accordance with the present invention, the article can be an air filter. Any article performing the air filtering function can be used as the air filter without special restrictions in kind, type, size and manufacturing process. Also, the type of the air filter can be appropriately modified depending on an apparatus using the filter without special restrictions. In accordance with the present invention, the air filter can replace a deodorization filter such as an activated charcoal filter, an aluminum mesh filter, a carbon filter, and a HEPA filter which are used in various electric home appliances such as a refrigerator, an air conditioner and an air freshener, and a filter of an air purifier of a vehicle, or can be used in combination with the existing filters.

In accordance with the present invention, the Kimchi lactic acid bacteria culture fluids acquired through various routes can be used without special restrictions, so far as they have the antibacterial and antivirus effects. For example, the Kimchi lactic acid bacteria culture fluid can be directly extracted from Kimchi, extracted from the cultivated Kimchi lactic acid bacteria, or purchased in a market. Any publicly-known method can be used to cultivate and extract the Kimchi lactic acid bacteria without special restrictions.

In addition, any phases of Kimchi lactic acid bacteria culture fluids can be used without special restrictions, so far as they have the antibacterial and antivirus effects. For example, the Kimchi lactic acid bacteria culture fluid can be selected from the group consisting of the Kimchi lactic acid bacteria culture fluid itself, a concentrate of the Kimchi lactic acid bacteria culture fluid, a dry matter of the Kimchi lactic acid bacteria culture fluid, and mixtures thereof. Any publicly-known method can be used to concentrate and dry the Kimchi lactic acid bacteria culture fluid without special restrictions.

Preferably, the Kimchi lactic acid bacteria are selected from the group consisting of *Leuconostoc* sp. Kimchi lactic acid bacteria, *Lactobacillus* sp. Kimchi lactic acid bacteria, *Weissella* sp. Kimchi lactic acid bacteria, and mixtures thereof.

Preferably, the *Leuconostoc* sp. Kimchi lactic acid bacteria are selected from the group consisting of *Leuconostoc citreum, Leuconostoc lactis, Leuconostoc mesenteroides* subsp. *dextranicum, Leuconostoc mesenteroides* subsp. *mesenteroides, Leuconostoc argentinum, Leuconostoc carnosum, Leuconostoc gellidum, Leuconostoc kimchii, Leuconostoc inhae, Leuconostoc gasicomitatum*, and mixtures thereof. More preferably, the *Leuconostoc* sp. Kimchi lactic acid bacteria are selected from the group consisting of *Leuconostoc citreum, Leuconostoc kimchii, Leuconostoc mesenteroides*, and mixtures thereof. Preferably, the *Lactobacillus* sp. Kimchi lactic acid bacteria are selected from the group consisting of *Lactobacillus brevis, Lactobacillus acidophilus, Lactobacillus bulgaricus, Lactobacillus plantarum, Lactobacillus kimchii, Lactobacillus paraplantarum, Lactobacillus curvatus* subsp. *curvatus, Lactobacillus sakei* subsp. *sakei*, and mixtures thereof.

Preferably, the *Weissella* sp. Kimchi lactic acid bacteria are selected from the group consisting of *Weissella koreensi, Weissella hanii, Weissella kimchii, Weissella soli, Weissella confusa*, and mixtures thereof.

In accordance with the present invention, the Kimchi lactic acid bacteria can be used with a binder. Silicone modified acryl resin, urethane resin, acryl resin and silicone resin, for example, can be used as the binder. That is, various kinds of binders can be employed. In the case that the Kimchi lactic acid bacteria are not singly used but used with the binder, the binder serves to easily fix the Kimchi lactic acid bacteria to the surface of the article, and improves the inter-coupling action between the surface of the article needing the antimicrobial property and the Kimchi lactic acid bacteria. As a result, the binder reduces the elution rate of the Kimchi lactic acid bacteria, and maintains the antimicrobial performance.

In accordance with the present invention, any kinds of metal particles having a sterilizing function can be used as the nano metal particles without special restrictions. Exemplary metal particles include Ag, Zn, Cu, Pt, Cd, Pd, Rh and Cr particles. The metal particles can be singly or mixedly used. The nano metal particles mean metal particles made in a nano size. Any kinds of metal particles made in a nano size can be used without special restrictions in manufacturing process. The nano metal particles prevent propagation of microorganisms such as bacteria, fungi, etc, by restricting the reproduction function of the microorganisms, and interrupt the metabolism of the microorganisms by infiltrating into cells and stopping the enzyme function required in respiration, thereby performing sterilization. In the viewpoint of the antibacterial property and harmlessness to the environment and human body, the nano metal particles are preferably Ag, Zn and Cu nano metal particles, more preferably, nano Ag. Especially, the nano Ag can improve the efficiency of the Kimchi lactic acid bacteria culture fluid.

In accordance with one aspect of the present invention, the Kimchi lactic acid bacteria culture fluid can be singly coated on the surface of the article, for giving the antimicrobial property. In accordance with another aspect of the present invention, both the Kimchi lactic acid bacteria culture fluid and the nano metal particles can be coated on the surface of the article, for giving the antimicrobial property. Expected is the synergy of the Kimchi lactic acid bacteria culture fluid with the antibacterial and antivirus effects and the nano metal particles with the antibacterial function. According to the characteristic of the article, the characteristic of the manufacturing process, and the necessity of the antimicrobial property, the Kimchi lactic acid bacteria culture fluid can be used singly or in combination with the nano metal particles. Preferably, 5 to 20 wt % of Kimchi lactic acid bacteria culture fluid and 100 to 2000 ppm of nano metal particles are coated on the surface of the article. This range semipermanently gives the antimicrobial property to the surface of the article in consideration of the antibacterial and antivirus effects over 99%, the coating characteristic and the mixing characteristic. However, if necessary, it can be appropriately adjusted.

The present invention also provides the manufacturing method of the article with the antimicrobial property which includes a step for coating the Kimchi lactic acid bacteria culture fluid or both the Kimchi lactic acid bacteria culture fluid and the nano metal particles on the surface of the article.

The step for coating the surface of the article with the Kimchi lactic acid bacteria culture fluid, or both the Kimchi lactic acid bacteria culture fluid and the nano metal particles can be performed according to a general method in the field to which the present invention pertains. Any kinds of methods which can evenly coat the surface of the article can be used.

When the Kimchi lactic acid bacteria culture fluid is singly coated, the Kimchi lactic acid bacteria culture fluid can be coated directly on the surface of the article. An appropriate fixation technique can be chemically or mechanically used to fix the Kimchi lactic acid bacteria culture fluid to the surface of the article. In addition, a method of preparing a coating solution containing the Kimchi lactic acid bacteria culture fluid, and spraying the coating solution to the surface of the article or dipping the article in the coating solution can be used to coat the surface of the article. The coating solution, for example, can be water or ethanol. Any solution containing the Kimchi lactic acid bacteria culture fluid at an appropriate amount and giving the antimicrobial property to the surface of the article by coating can be used as the coating solution without special restrictions in kind and manufacturing process. The publicly-known spraying method such as air spray can be used, which is not intended to be limiting. Any kinds of methods which can evenly coat the surface of the article can be employed. In addition, the general dipping method can be used without special restrictions. Preferably, the amount of the Kimchi lactic acid bacteria culture fluid ranges from 5 to 20 wt %, which is not intended to be limiting. If necessary, the amount of the Kimchi lactic acid bacteria culture fluid can be appropriately adjusted.

Alternatively, in the case that the Kimchi lactic acid bacteria culture fluid and the nano metal particles are coated together, the Kimchi lactic acid bacteria culture fluid and the nano metal particles can be sequentially coated on the surface of the target article. According to the sequential coating process, the nano metal particles are coated on the surface of the article, and then the Kimchi lactic acid bacteria culture fluid is coated on the surface of the article coated with the nano metal particles. The step for coating the nano metal particles on the surface of the article can be performed according to a method publicly known in this field. If necessary, the nano metal particles can be modified for easy coating depending on the characteristic of the article. In addition, the step for coating the Kimchi lactic acid bacteria culture fluid on the surface of the article coated with the nano metal particles can be performed according to a method generally used in this field without special restrictions. A chemical or mechanical method can be appropriately used to fix the Kimchi lactic acid bacteria to the article coated with the nano metal particles. Any method of evenly coating the surface of the article, such as spraying and dipping can be used for coating. Conversely, it is possible to be coated with the Kimchi lactic acid bacteria culture fluid first, and coated with the nano metal particles on the surface of the article coated with the Kimchi lactic acid bacteria culture fluid. It is also possible to prepare a coating solution containing the Kimchi lactic acid bacteria culture fluid and the nano metal particles by mixing the two substances, and coat the coating solution on the surface of the article by spraying or dipping. Any method of preparing the coating solution can be employed without special restrictions, so far as the Kimchi lactic acid bacteria culture fluid and the nano metal particles can be coated on the surface of the article to give the antimicrobial property. Preferably, the amount of the Kimchi lactic acid bacteria culture fluid ranges from 5 to 20 wt %, and the content of the nano metal particles ranges from 100 to 2000 ppm. This range semipermanently gives the antimicrobial property to the surface of the article in consideration of the antibacterial and antivirus effects over 99%, the coating characteristic and the mixing characteristic. However, if necessary, this range can be appropriately adjusted.

Further, in accordance with the present invention, in the case that the Kimchi lactic acid bacteria culture fluid is coated on the surface of the article, the Kimchi lactic acid bacteria culture fluid can be mixed with the binder before the coating step. The binder improves the inter-coupling action between the surface of the article and the Kimchi lactic acid bacteria culture fluid, and reduces the elution rate of the Kimchi lactic acid bacteria culture fluid, thereby maintaining the antimicrobial performance. Accordingly, it is more advantageous to mix the Kimchi lactic acid bacteria culture fluid with the binder than to singly use the Kimchi lactic acid bacteria culture fluid. Any method of mixing the Kimchi lactic acid bacteria culture fluid with the binder can be used without special restrictions, so far as the Kimchi lactic acid bacteria culture fluid can be coated on the surface of the article. The content ratio of the Kimchi lactic acid bacteria culture fluid to the binder is not specially restricted but appropriately adjusted. If necessary, an inorganic pigment can be added.

In accordance with one embodiment of the present invention, the coating solution containing the Kimchi lactic acid bacteria culture fluid and the nano metal particles was prepared, and spray-coated on an aluminum mesh filter, thereby obtaining the filter with the antimicrobial property. In one experiment of the present invention, *Escherichia coli, Staphyllococcus aureus* and *Pseudomonas aeruginosa* were used to test the antibacterial activity of the filter with the antimicrobial property. As a result, the filter with the antimicrobial property showed excellent antibacterial activity to *Escherichia coli, Staphyllococcus aureus* and *Pseudomonas aeruginosa*. In another experiment of the present invention, H5N1, which was an avian influenza virus, was used to test the antivirus activity of the filter. As a result, the filter showed a high virus reduction rate.

On the other hand, the manufacturing method can further include a step for washing the target article with proper wash water, and a step for drying the article by a thermal treatment after the washing, prior to coating the Kimchi lactic acid bacteria culture fluid on the surface of the article. In addition, the manufacturing method can further include a step for drying the article naturally or by a thermal treatment after coating the Kimchi lactic acid bacteria culture fluid on the surface of the article. The thermal treatment serves to fix the Kimchi lactic acid bacteria culture fluid and the nano metal particles to the surface of the article. A drying time and a drying temperature of the article are adjustable according to the shape, kind and size of the article. In case the target article is made of metal, it is advantageous to remove oil elements sticking to the surface of the article in the manufacturing or keeping process.

In accordance with the present invention, if necessary, the manufactured article can be post-processed into a wanted shape and appropriately used. Especially, the air filter can be cut into a wanted size and used as a filter of an air purifier. The air filter can be used singly or in combination with the existing air filter and deodorization filter in the same product. The air filter can be applied to various air purifiers for home or business use, refrigerators, vehicles, and other electric home appliances.

The present invention will now be explained by the following examples. Such examples are not intended to be limiting.

Example 1

An aluminum mesh made by Airphil corporation was immersed into 2.5 NaOH solution for about 3 minutes, to remove oil components. Then, the oil removed-aluminum mesh was washed with 2.5% NaOH solution. The washing step was repeated 7 times. A thermal treatment was performed on the washed aluminum mesh by drying in a dry oven at a temperature of 40° C. for 2 hours.

Example 2

10 g of dry powder of culture fluid of *Leuconostoc citreum* selected from the *Leuconostoc* sp. Kimchi lactic acid bacteria was mixed with 15 g of silicone modified acryl resin binder, 3 g of nano zinc, 1 g of nano silver and 0.5 g of nano copper, and dissolved in a water as a solvent, thereby preparing a coating solution containing Kimchi lactic acid bacteria culture fluid. The coating solution was air-sprayed on the aluminum mesh prepared in Example 1 and then the coated aluminum mesh was dried. Obtained was an aluminum mesh filter sample coated with the Kimchi lactic acid bacteria culture fluid and the nano metal particles.

Test Example 1

Antibacterial Property Test

The antibacterial property of the aluminum mesh coated with the Kimchi lactic acid bacteria culture fluid in Example 2 was tested according to a shake flask method (KS M 0146-2003) by using *Escherichia coli* (ATCC 25922), *Staphylococcus aureus* (ATCC 6538) and *Pseudomonas aeruginosa* (ATCC 27853).

1 ml of *Escherichia coli* culture, *Staphylococcus aureus* culture and *Pseudomonas aeruginosa* culture were coated on the aluminum mesh filter samples (1.0 cm×1.0 cm) prepared in Example 2, respectively. The aluminum mesh filter samples coated with each strain culture were immersed into a Erlenmeyer flask containing LB broth, and shake incubated at 35±1° C. in 120 rpm for 3 hours. For comparison, 1 ml of each strain culture was inoculated into a Erlenmeyer flask containing LB broth, and shake incubated in the same condition. The incubated cell cultures were taken up to spread on a LB plate, and incubated at 37° C. for 48 hours. The colonies of each bacteria were counted. The results are shown in the following Tables 1 to 3.

TABLE 1

| Strain | Sample | Initial (cfu/ml) | 1 hr (cfu/ml) | 2 hrs. (cfu/ml) | 3 hrs. (cfu/ml) | Suppression rate (%) |
|---|---|---|---|---|---|---|
| *E. coli* | Example 2 | $1.5 \times 10^5$ | <10 | <10 | <10 | >99.9 |
|  | Comparison | $1.5 \times 10^5$ | $1.6 \times 10^5$ | $1.7 \times 10^5$ | $2.0 \times 10^5$ |  |

*cfu/ml: colony formation unit per ml

TABLE 2

| Strain | Sample | Initial (cfu/ml) | 1 hr (cfu/ml) | 2 hrs. (cfu/ml) | 3 hrs. (cfu/ml) | Suppression rate (%) |
|---|---|---|---|---|---|---|
| *S. aureus* | Example 2 | $1.5 \times 10^5$ | <10 | <10 | <10 | >99.9 |
|  | Comparison | $1.3 \times 10^5$ | $1.5 \times 10^5$ | $1.8 \times 10^3$ | $2.2 \times 10^5$ |  |

*cfu/ml: colony formation unit per ml

TABLE 3

| Strain | Sample | Initial No. (cfu/ml) | 1 hr (cfu/ml) | 2 hrs. (cfu/ml) | 3 hrs. (cfu/ml) | Suppression rate (%) |
|---|---|---|---|---|---|---|
| *P. aeruginosa* | Example 2 | $1.2 \times 10^5$ | <10 | <10 | <10 | >99.9 |
|  | Comparison | $1.2 \times 10^5$ | $1.4 \times 10^5$ | $1.7 \times 10^5$ | $2.2 \times 10^5$ |  |

*cfu/ml: colony formation unit per ml

As known from the above Tables 1 to 3, as compared with the comparisons, the aluminum mesh filter coated with the Kimchi lactic acid bacteria culture fluid has excellent antibacterial activity to microorganisms, such as *Escherichia coli*, *Staphylococcus aureus* and *Pseudomonas aeruginosa*.

Test Example 2

Antivirus Property Test

A coating solution containing Kimchi lactic acid bacteria culture fluid was prepared and sprayed on surfaces of an aluminum mesh filter, a carbon filter and a HEPA filter, respectively, thereby obtaining three kinds of filter samples coated with the Kimchi lactic acid bacteria culture fluid. The antivirus property test was performed on each filter.

Avian influenza virus H5N1 isolate was used to test the antivirus effect of the Kimchi lactic acid bacteria culture fluid. Mardin-Darby Canine Kidney (MDCK) cell lines from dog kidney cells were used as host cells of viruses.

First, 100 µl of MDCK cells ($5 \times 10^4$ cells/ml) were seeded onto each well of a 96-well plate, and incubated in 5% $CO_2$ incubator at 37° C. for 24 hours, so that the cells could cover the bottoms of the wells in a monolayer shape. A virus solution (1/10 v/v) diluted with PBS was added to each well containing the three kinds of samples (aluminum mesh filter, carbon filter and HEPA filter, respectively) coated with the Kimchi lactic acid bacteria culture fluid, and incubated at 37° C. For comparison, the virus solution was incubated in the same manner in regard to the same three samples which were not coated with the Kimchi lactic acid bacteria culture fluid. The weight of each sample was recorded before addition of the virus solution. A culture inoculated with the virus solution and a culture which was not inoculated with the virus solution were prepared for a positive comparison and a negative comparison to the viral cytopathic effect (vCPE), respectively.

In order to test the antivirus effect, the 10-times diluted culture for the aluminum filter sample coated with the Kimchi lactic acid bacteria culture fluid, the aluminum filter sample which was not coated with the Kimchi lactic acid bacteria culture fluid, and the positive comparison was inoculated into the seven rows of the 96-well plates in quadruple. And the culture for the negative comparison was inoculated into the final eighth row. After the inoculation, the plates were incubated in 5% $CO_2$ incubator at 37° C. for 3 days. The vCPE of the plate was observed, and the virus titer was determined as $TCID_{50}$ (50% tissue culture infective dose). The antivirus effect was represented by a virus reduction rate (%). Here, the virus reduction rate was a percentage value of $-\log TCID_{50}/ml$ converted by using a value obtained by subtracting the weight of the sample which was not coated with the Kimchi lactic acid bacteria culture fluid from the weight of the sample coated with the Kimchi lactic acid bacteria culture fluid. The results are shown in the following Tables 4 to 6.

TABLE 4

| | Virus titer ($TCID_{50}/ml$) | Coated Al mesh filter (g) | Non-coated Al mesh filter (g) | Virus reduction rate (%) |
|---|---|---|---|---|
| 30 minutes | 6.25 | 0.1132 | 0.0946 | 99.92 |
| 1 hour | 6.50 | 0.1091 | 0.0871 | >99.99 |
| 2 hours | 6.27 | 0.0999 | 0.0809 | >99.99 |
| 4 hours | 6.25 | 0.1195 | 0.0872 | >99.99 |
| 8 hours | 5.75 | 0.1175 | 0.0806 | 99.99 |

TABLE 5

| | Virus titer ($TCID_{50}/ml$) | Coated C filter (g) | Non-coated C filter (g) | Virus reduction rate (%) |
|---|---|---|---|---|
| 30 minutes | 6.75 | 0.3194 | 0.2720 | 99.90 |
| 1 hour | 6.50 | 0.3240 | 0.2743 | 99.84 |
| 2 hours | 6.00 | 0.3196 | 0.2635 | >99.99 |
| 4 hours | 5.75 | 0.4346 | 0.2887 | 99.82 |

TABLE 6

| | Virus titer ($TCID_{50}/ml$) | Coated HEPA filter (g) | Non-coated HEPA filter (g) | Virus reduction rate (%) |
|---|---|---|---|---|
| 30 minutes | 6.00 | 0.0820 | 0.0614 | 98.22 |
| 1 hour | 5.75 | 0.0848 | 0.0678 | 99.82 |
| 2 hours | 6.50 | 0.0545 | 0.0514 | 99.94 |
| 4 hours | 6.25 | 0.0560 | 0.0486 | 99.99 |
| 8 hours | 5.75 | 0.0529 | 0.0461 | 99.99 |

As known from the above Tables 4 to 6, the aluminum mesh filter, the carbon filter and the HEPA filter coated with the Kimchi lactic acid bacteria culture fluid have the virus reduction rate almost over 99%, namely, the excellent antivirus effect.

Application Examples

In accordance with the present invention, the article can be used for various uses. The electric home appliances needing the antimicrobial property are a refrigerator, washing machine, air conditioner, cleaner, air freshener, water purifier, humidifier, dishwashing machine, microwave oven, VTR, computer, television, etc.

1) Application to Refrigerator

The present invention can be applied to an inner wall, a cool air duct, a ventilation fan, a door handle, a vegetable box, an air filter, an ice maker, a basket, and an outer surface of the refrigerator.

2) Application to Washing Machine

The surfaces of the parts of the washing machine such as an inner tub, an outer tub, a pulsator, a detergent box, a drum lift and a tub can be coated. The present invention can be applied to filters (air filter and water filter) in a dry passage, a water supply/drain passage, and a circulation passage.

3) Application to Air Conditioner

The present invention can be applied to fins of a heat exchanger, an electric heat exchanger (ventilation element), a ventilation fan (metal and molded matter), an air passage (suction unit, discharge unit, louvers, grill, etc.), and an air filter of an indoor unit.

4) Application to Air Freshener

A special Kimchi lactic acid bacteria culture fluid filter can be mounted as one of multiple filters of the air freshener.

5) Application to Cleaner

The user often touches the cleaner with his/her hands. Therefore, the surface of the cleaner can be coated. The sterilization effect can be improved by coating an inside of a dust container. The present invention can also be applied to an exhaust filter of the cleaner.

6) Application to Dishwashing Machine

The present invention can be applied to a tub, a sump, a screen, a spray arm, a water filter, etc.

Although the preferred embodiments of the present invention have been described, it is understood that the present invention should not be limited to these preferred embodi-

INDUSTRIAL APPLICABILITY

As discussed earlier, in accordance with the present invention, the article needing the antimicrobial effect is provided with the antimicrobial property, by coating the Kimchi lactic acid bacteria culture fluid with the wide antibacterial spectrum singly or in combination with the nano metal particles. The article is also provided with the antivirus property to avian influenza viruses and other viruses with the similar mechanism to that of avian influenza viruses due to the excellent antivirus activity of the Kimchi lactic acid bacteria culture fluid.

The invention claimed is:

1. An article with an antimicrobial property comprising a coating with both Kimchi lactic acid bacteria culture fluid originated from Kimchi lactic acid bacteria and nano metal particles,
wherein the nano metal particles are selected from the group consisting of Ag, Zn, Cu, Pt, Cd, Pd, Rh, Cr, and mixtures thereof.

2. The article with the antimicrobial property of claim 1, wherein the Kimchi lactic acid bacteria culture fluid is selected from the group consisting of the Kimchi lactic acid bacteria culture fluid itself, a concentrate of the Kimchi lactic acid bacteria culture fluid, a dry matter of the-Kimchi lactic acid bacteria culture fluid, and mixtures thereof.

3. The article with the antimicrobial property of claim 1, wherein the Kimchi lactic acid bacteria are selected from the group consisting of *Leuconostoc* sp. Kimchi lactic acid bacteria, *Lactobacillus* sp. Kimchi lactic acid bacteria, *Weissella* sp. Kimchi lactic acid bacteria, and mixtures thereof.

4. The article with the antimicrobial property of claim 3, wherein the *Leuconostoc* sp. Kimchi lactic acid bacteria are selected from the group consisting of *Leuconostoc citreum, Leuconostoc lactis, Leuconostoc mesenteroides* subsp. *dextranicum, Leuconostoc mesenteroides* subsp. *mesenteroides, Leuconostoc argentinum, Leuconostoc carnosum, Leuconostoc gellidum, Leuconostoc kimchii, Leuconostoc inhae, Leuconostoc gasicomitatum*, and mixtures thereof.

5. The article with the antimicrobial property of claim 3, wherein the *Lactobacillus* sp. Kimchi lactic acid bacteria are selected from the group consisting of *Lactobacillus brevis, Lactobacillus acidophilus, Lactobacillus bulgaricus, Lactobacillus plantarum, Lactobacillus kimchii, Lactobacillus paraplantarum, Lactobacillus curvatus* subsp. *curvatus, Lactobacillus sakei* subsp. *sakei*, and mixtures thereof.

6. The article with the antimicrobial property of claim 3, wherein the *Weissella* sp. Kimchi lactic acid bacteria are selected from the group consisting of *Weissella koreensi, Weissella hanii, Weissella kimchii, Weissella soli, Weissella confusa*, and mixtures thereof.

7. The article with the antimicrobial property of claim 1, wherein the nano metal particles are selected from the group consisting of Ag, Zn, Cu, and mixtures thereof.

8. The article with the antimicrobial property of claim 1, which is one of the whole electric home appliances or the internal or external parts of the electric home appliances, such as a refrigerator, washing machine, drying machine, air conditioner, air freshener, fan, cleaner, electric pot, electric cooker, dishwashing machine, dish drying machine, water purifier, microwave oven, mixer, VTR, television and home theater.

9. The article with the antimicrobial property of claim 1, which is a filter.

10. The article with the antimicrobial property of claim 9, wherein the material of the filter is selected from the group consisting of a glass fiber, an ion exchange fiber, a cellulose fiber and an asbestos fiber.

11. The article with the antimicrobial property of claim 9, wherein the material of the filter is a metal or a plastic.

12. The article with the antimicrobial property of claim 9, wherein the type of filter is selected from the group consisting of honeycomb type, grain type, net type, filter paper type, cotton type, mesh type, plate type or foam type.

13. The article with the antimicrobial property of claim 9, wherein the filter is an air cleaning filter.

14. The article with the antimicrobial property of claim 1, further comprising a binder selected from the group consisting of silicone modified acryl resin, urethane resin, acryl resin and silicone resin.

15. An article with an antimicrobial property comprising a coating with both Kimchi lactic acid bacteria culture fluid originated from Kimchi lactic acid bacteria and nano metal particles,
wherein the Kimchi lactic acid bacteria culture fluid is coated in the range of 5 to 20 wt %, and the nano metal particles are coated in the range of 100 to 2000 ppm.

16. A manufacturing method of an article with an antimicrobial property as recited in claim 1, comprising a step for coating both the Kimchi lactic acid bacteria culture fluid and nano metal particles on the surface of the article,
wherein the coating step comprise a sequential step for coating the nano metal particles on the surface of the article and then coating the Kimchi lactic acid bacteria culture fluid on the surface of the article coated with the nano metal particles.

17. The manufacturing method of claim 16, wherein the coating step comprises a step for spraying a coating solution containing both the Kimchi lactic acid bacteria culture fluid and nano metal particles to the surface of the article, or dipping the article in the coating solution.

18. The manufacturing method claim 16, further comprising a step for mixing a binder selected from the group consisting of silicone modified acryl resin, urethane resin, acryl resin and silicone resin with the Kimchi lactic acid bacteria culture fluid prior to the coating step.

19. The article with the antimicrobial property of claim 2, wherein the Kimchi lactic acid bacteria are selected from the group consisting of *Leuconostoc* sp. Kimchi lactic acid bacteria, *Lactobacillus* sp. Kimchi lactic acid bacteria, *Weissella* sp. Kimchi lactic acid bacteria, and mixtures thereof.

20. The article with the antimicrobial property of claim 19, wherein the *Leuconostoc* sp. Kimchi lactic acid bacteria are selected from the group consisting of *Leuconostoc citreum, Leuconostoc lactis, Leuconostoc mesenteroides* subsp. *dextranicum, Leuconostoc mesenteroides* subsp. *mesenteroides, Leuconostoc argentinum, Leuconostoc carnosum, Leuconostoc gellidum, Leuconostoc kimchii, Leuconostoc inhae, Leuconostoc gasicomitatum*, and mixtures thereof.

21. The article with the antimicrobial property of claim 19, wherein the *Lactobacillus* sp Kimchi lactic acid bacteria are selected from the group consisting of *Lactobacillus brevis, Lactobacillus acidophilus, Lactobacillus bulgaricus, Lactobacillus plantarum, Lactobacillus kimchii, Lactobacillus paraplantarum, Lactobacillus curvatus* subsp. *curvatus, Lactobacillus sakei* subsp. *sakei*, and mixtures thereof.

22. The article with the antimicrobial property of claim 19, wherein the *Weissella* sp. Kimchi lactic acid bacteria are selected from the group consisting of *Weissella koreensi,*

*Weissella hanii, Weissella kimchii, Weissella soli, Weissella confusa*, and mixtures thereof.

23. The manufacturing method of claim 17, further comprising a step for mixing a binder selected from the group consisting of silicone modified acryl resin, urethane resin, acryl resin and silicone resin with the Kimchi lactic acid bacteria culture fluid prior to the coating step.

24. The manufacturing method of claim 16, further comprising a step for mixing a binder selected from the group consisting of silicone modified acryl resin, urethane resin, acryl resin and silicone resin with the Kimchi lactic acid bacteria culture fluid prior to the coating step.

* * * * *